United States Patent
Neumann

(10) Patent No.: US 11,700,128 B2
(45) Date of Patent: Jul. 11, 2023

(54) METHODS AND SYSTEMS FOR CRYPTOGRAPHICALLY SECURED OUTPUTS FROM TELEMEDICINE SESSIONS

(71) Applicant: KPN INNOVATIONS, LLC., Lakewood, CO (US)

(72) Inventor: Kenneth Neumann, Lakewood, CO (US)

(73) Assignee: KPN INNOVATIONS, LLC., Lakewood, CO (US)

(*) Notice: Subject to any disclaimer, the term of this patent is extended or adjusted under 35 U.S.C. 154(b) by 187 days.

(21) Appl. No.: 17/164,435

(22) Filed: Feb. 1, 2021

(65) Prior Publication Data
US 2022/0060333 A1 Feb. 24, 2022

Related U.S. Application Data

(63) Continuation of application No. 17/000,889, filed on Aug. 24, 2020, now Pat. No. 11,005,661.

(51) Int. Cl.
| | |
|---|---|
| *H04L 9/32* | (2006.01) |
| *G06N 20/00* | (2019.01) |
| *G16H 80/00* | (2018.01) |
| *G16H 10/60* | (2018.01) |

(52) U.S. Cl.
CPC ........... *H04L 9/3231* (2013.01); *G06N 20/00* (2019.01); *G16H 10/60* (2018.01); *G16H 80/00* (2018.01); *H04L 9/3297* (2013.01)

(58) Field of Classification Search
CPC ..... H04L 9/3231; H04L 9/3297; H04L 9/324; H04L 9/07; H04L 63/0861; H04L 63/126; H04L 2209/88; G06N 20/00; G06N 3/0454; G06N 3/08; G06N 7/005; G16H 10/60; G16H 80/00; G16H 40/67
See application file for complete search history.

(56) References Cited

U.S. PATENT DOCUMENTS

| | | |
|---|---|---|
| 7,483,839 B2 | 1/2009 | Mayaud |
| 2006/0259330 A1 | 11/2006 | Schranz |
| 2009/0157424 A1 | 6/2009 | Hans |

(Continued)

OTHER PUBLICATIONS https://www.researchgate.net/profile/Mohamad_Sadikin3/publication/314667530_Implementing_digital_signature_for_the_secure_electronic_prescription_using_QRcode_based_on_Android_smartphone/links/59d49ef2a6fdcc181adc3c10/Implementing-digital-signature-for-the-secure-electronic-prescription-using-QR-code-based-on-Android-smartphone.pdf; Date: Aug. 2016; By: Mohamad Ali Sadikin.

(Continued)

*Primary Examiner* — Khoi V Le

(74) *Attorney, Agent, or Firm* — Caldwell Intellectual Property Law

(57) ABSTRACT

A system for cryptographically secured outputs from telemedicine sessions includes a computing device at a first location, the computing device configured to initiate a secure communication interface between the computing device and a client device associated with a human subject and at a second location, receive, from at least a remote sensor at the second location, a plurality of current biological data associated with the human subject, input, using the secure communication interface, an identifier of a biochemical element, determine, as a function of the plurality of current biological data, a tolerability of the biochemical element, and generate a digitally signed authorization datum as a function of the determination.

18 Claims, 6 Drawing Sheets

(56) References Cited

U.S. PATENT DOCUMENTS

| | | |
|---|---|---|
| 2010/0169218 A1 | 7/2010 | Wang et al. |
| 2010/0268550 A1* | 10/2010 | Abuzeni ............... G16H 20/10 |
| | | 705/2 |
| 2013/0060576 A1* | 3/2013 | Hamm .................. G16H 40/67 |
| | | 705/2 |
| 2013/0231945 A1* | 9/2013 | Barry .................... G16H 40/67 |
| | | 705/2 |
| 2016/0323165 A1* | 11/2016 | Boucadair .............. H04L 43/12 |
| 2016/0378949 A1 | 12/2016 | Fu et al. |
| 2017/0300654 A1* | 10/2017 | Stein ....................... H01Q 1/42 |
| 2017/0323074 A1* | 11/2017 | Chiang ................. H04N 7/147 |
| 2018/0192965 A1* | 7/2018 | Rose ...................... G16H 80/00 |
| 2019/0109830 A1 | 4/2019 | McFarland et al. |
| 2019/0237176 A1 | 8/2019 | O'brien et al. |
| 2019/0272908 A1 | 9/2019 | Hill |
| 2019/0378599 A1 | 12/2019 | Amisano et al. |
| 2020/0135317 A1 | 4/2020 | Karbowicz et al. |

OTHER PUBLICATIONS https://www.researchgate.net/profile/Rania_Baashirah/publication/328968499_Improve_Healthcare_Safety_Using_Hash-Based_Authentication_Protocol_for_RFID_Systems/links/5bede82192851c6b27c24e81/Improve-Healthcare-Safety-Using-Hash-Based-Authentication-Protocol-for-RFID-Systems.pdf; By: Rania Baashirah; Nov. 2018.

https://www.dovepress.com/front_end/cr_data/cache/pdf/download_1594911810_5f106c429d5e8/AHCT-64477-electronic-prescriptions—opportunities-and-challenges-for-t_020316.pdf; Date: 2016; By: Ashley E Lanham.

\* cited by examiner

METHODS AND SYSTEMS FOR CRYPTOGRAPHICALLY SECURED OUTPUTS FROM TELEMEDICINE SESSIONS

CROSS-REFERENCE TO RELATED APPLICATIONS

This application is a continuation of Non-provisional Application Ser. No. 17/000,889 filed on Aug. 24, 2020 and entitled "METHODS AND SYSTEMS FOR CRYPTOGRAPHICALLY SECURED OUTPUTS FROM TELEMEDICINE SESSIONS," the entirety of which is incorporated herein by reference.

FIELD OF THE INVENTION

The present invention generally relates to the field of network communication. In particular, the present invention is directed to cryptographically secured outputs from telemedicine sessions.

BACKGROUND

Network connections can be susceptible to attack, leading to publication of private and sensitive information. Frequently, this can leave users unable to securely communicate, particularly in situations in need of immediate attention. This may have subsequent effects on reliability of data elements generated therefrom.

SUMMARY OF THE DISCLOSURE

In an aspect, a system for telemedicine prescription through remote sensing includes a computing device designed and configured to initiate a secure communication interface between the computing device and a client device associated with a human subject and at a second location, receive, from at least a remote sensor at the second location, a plurality of current physiological data associated with the human subject, input, using the secure communication interface, an identifier of a pharmaceutical element, wherein inputting further includes identifying a plurality of pharmaceutical elements as a function of the plurality of current physiological data, displaying the plurality of pharmaceutical elements to a user of computing device, and receiving a command from a user of the computing device selecting a pharmaceutical element of the plurality of pharmaceutical elements, determine, as a function of the plurality of current physiological data, a tolerability of the pharmaceutical element, and generate a digitally signed prescription as a function of the determination.

In another aspect, a method of telemedicine prescription through remote sensing includes initiating, by a computing device at a first location, a secure communication interface between the computing device and a client device associated with a human subject and at a second location, receiving, by the computing device and from at least a remote sensor at the second location, a plurality of current physiological data associated with the human subject, inputting, by the computing device and using the secure communication interface, an identifier of a pharmaceutical element, wherein inputting further includes identifying a plurality of pharmaceutical elements as a function of the plurality of current physiological data, displaying the plurality of pharmaceutical elements to a user of computing device, and receiving a command from a user of the computing device selecting a pharmaceutical element of the plurality of pharmaceutical elements, determining, by the computing device and as a function of the plurality of current physiological data, a tolerability of the pharmaceutical element and generating a digitally signed prescription as a function of the determination.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

Embodiments disclosed herein generate cryptographically secured outputs from using a secure communication interface supporting a telemedicine session. Embodiments may perform identity verification on both a human subject and on biological data presented as pertaining thereto, which may aid in both assurance of a correctly ascribed output and a valid tolerance evaluation.

Figure 1:
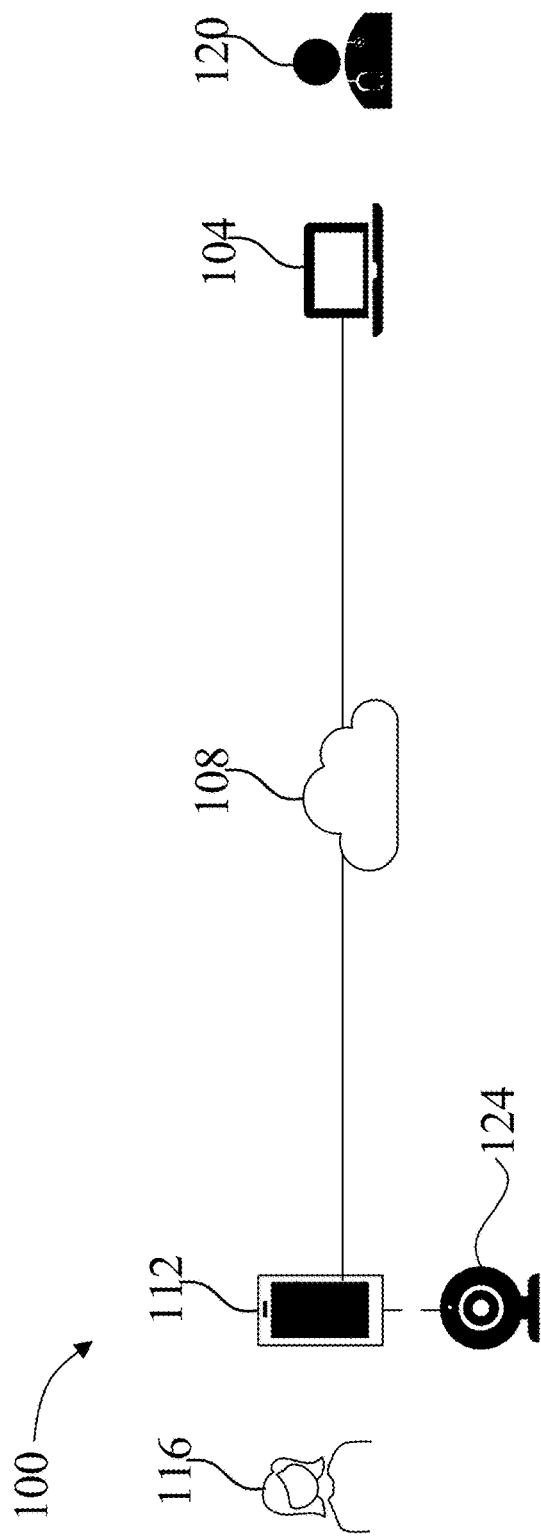
FIG. 1 is a schematic diagram of an exemplary embodiment of a system for cryptographically secured outputs from telemedicine sessions.

Referring now to FIG. 1, an exemplary embodiment of system 100 for cryptographically secured outputs from telemedicine sessions is illustrated. System includes a computing device 104. Computing device 104 may include any computing device 104 as described in this disclosure, including without limitation a microcontroller, microprocessor, digital signal processor (DSP) and/or system on a chip (SoC) as described in this disclosure. Computing device 104 may include, be included in, and/or communicate with a mobile device such as a mobile telephone or smartphone. Computing device 104 may include a single computing device 104 operating independently or may include two or more computing device 104 operating in concert, in parallel, sequentially or the like; two or more computing devices may be included together in a single computing device 104 or in two or more computing devices. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device 104. Computing device 104 may include but is not limited to, for example, a computing device 104 or cluster of computing devices in a first location and a second computing device 104 or cluster of computing devices in a second location. Computing device 104 may include one or more computing devices dedicated to data storage, security, distribution of traffic for load balancing, and the like. Computing device 104 may distribute one or more computing tasks as described below across a plurality of computing devices of computing device 104, which may operate in parallel, in series, redundantly, or in any other manner used for distribution of tasks or memory between computing devices. Computing device 104 may be implemented using a "shared nothing" architecture in which data is cached at the worker, in an embodiment, this may enable scalability of system 100 and/or computing device 104.

Computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Still referring to FIG. 1, computing device 104 may be configured to initiate a communication channel interface between the computing device 104 and a client device 112 operated by a human subject 116. A "human subject," as used in this disclosure, is a person at a client device 112 receiving telemedicine services such as a virtual doctor's visit, physical, "checkup," or the like. A "communication channel interface," as used in this disclosure, is a communication medium within an interface. A communication channel interface may include an application, script, and/or program capable of providing a means of communication between at least two parties, including any oral and/or written forms of communication. A communication channel interface may allow computing device 104 to interface with electronic devices through graphical icons, audio indicators including primary notation, text-based user 120 interfaces, typed command labels, text navigation, and the like. A communication channel interface may include slides or other commands that may allow a user 120 to select one or more options. A communication channel interface may include free form textual entries, where a user 120 may type in a response and/or message. A communication channel interface includes a display interface. Display interface includes a form or other graphical element having display fields, where one or more elements of information may be displayed. Display interface may display data output fields including text, images, or the like containing one or more messages. A communication channel interface may include data input fields such as text entry windows, drop-down lists, buttons, checkboxes, radio buttons, sliders, links, or any other data input interface that may capture user 120 interaction as may occur to persons skilled in the art upon reviewing the entirety of this disclosure. A communication channel interface may be provided, without limitation, using a web browser, a native application, a mobile application, and the like.

With continued reference to FIG. 1, computing device 104 initiates a communication channel interface with a client device 112. A "client device," as used in this disclosure, is a second computing device 104, including for example a mobile device such as a smartphone, tablet, laptop, desktop, and/or any other type of device suitable for use as computing device 104. Client device 112 is operated by a human subject 116; human subject 116 may include a person to whom telemedicine services are being rendered, including without limitation a patient. Computing device 104 may initiate communication channel interface using any network methodology as described herein. In an embodiment, a communication channel interface may be utilized to facilitate communications between a client device 112 operated by a human subject 116, and computing device 104 which may be operated by a user 120; user 120 may include a doctor, nurse, nurse practitioner, medical technician, medical assistant, pharmacist, pharmacy technician, and/or any other medical professional. For example, client device 112 may be operated by a patient who is in communication with a medical professional operating computing device 104, and communication channel interface may be utilized to have a telemedicine appointment. In yet another non-limiting example, client device 112 may be operated by a first member of a support group, and computing device 104 may be operated by a second member of the support group, whereby communication channel interface may be utilized to facilitate support group meetings and secure communications between members of the support group.

Further referring to FIG. 1, display interface may include a secure display interface, which may be implemented, maintained, and/or validated according to any process as described in U.S. Nonprovisional application Ser. No. 16/919,674, filed on Jul. 2, 2020, and entitled "METHODS AND SYSTEMS FOR GENERATING A SECURE COMMUNICATION CHANNEL INTERFACE FOR STREAM- ING OF SENSITIVE CONTENT," the entirety of which is incorporated herein by reference.

With continued reference to FIG. 1, an as a non-limiting example, initiating a secure communication channel interface 108 may include transmitting to user 120 client device 112 a configuration packet uniquely identifying computing device 104. A "configuration packet," as used in this disclosure, is an encrypted message including a non-public device identifier." An encrypted message includes any language that contains text, characters, and/or symbols that have been converted into an alternative form, such as but not limited to ciphertext. An encrypted message may include using an algorithm and/or a series of algorithms to transform plaintext messages into ciphertext. Encrypted messages may only be viewed in a non-encrypted from by decrypting it using a correct decryption key. Encrypted messages may be decrypted using both symmetric and asymmetric cryptographic key pairs, such as for example a public and private key pair. An encrypted message may be generated in a manner that complies with the Health Insurance Portability and Accountability Act (HIPPA) of 1996. A message may be encrypted using a pseudo-random encryption key generated by an algorithm. In one embodiment, a process of converting plaintext into ciphertext is known as "encryption." Encryption process may involve the use of a datum, known as an "encryption key," to alter plaintext. Cryptographic system may also convert ciphertext back into plaintext, which is a process known as "decryption." Decryption process may involve the use of a datum, known as a "decryption key," to return the ciphertext to its original plaintext form. In embodiments of cryptographic systems that are "symmetric," decryption key is essentially the same as encryption key: possession of either key makes it possible to deduce the other key quickly without further secret knowledge. Encryption and decryption keys in symmetric cryptographic systems may be kept secret and shared only with persons or entities that the user 120 of the cryptographic system wishes to be able to decrypt the ciphertext. One example of a symmetric cryptographic system is the Advanced Encryption Standard ("AES"), which arranges plaintext into matrices and then modifies the matrices through repeated permutations and arithmetic operations with an encryption key.

With continued reference to FIG. 1, a "non-public device identifier," as used in this disclosure, is a decryption key that cannot be readily deduced without additional secret knowledge, such as for example, a private key. A non-public device identifier may include a randomly generated number that cannot be easily guessed. A non-public device identifier may be generated using a stream cipher and/or a block cipher. An encrypted message may be transmitted with a non-public device identifier, to initiate secure communication between computing device 104 and user 120 client device 112.

With continued reference to FIG. 1, computing device 104 may receive from user 120 device 104 a confirmation authentication a configuration packet. A confirmation may include any message, that allows user 120 client device 112 to confirm the identify and/or authenticity of computing device 104. A confirmation may be transmitted from user 120 client device 112 to computing device 104 using any network methodology as described herein. In an embodiment, a confirmation authentication may include receiving from user 120 client device 112 a configuration packet uniquely identifying user 120 client device 112. In such an instance, computing device 104 may receive the configuration packet uniquely identifying user 120 client device 112 and authenticate the configuration packet, and the identify of user 120 client device 112. Computing device 104 establishes a communication exchange as a function of receiving from user 120 client device 112, a confirmation authenticating the configuration packet. A communication exchange includes any telecommunication handshake that includes an automated process of communications between two or more participants, such as computing device 104 and user 120 client device 112. A telecommunication handshake includes the exchange of information establishing protocols of communication at the start of communication before full communication commences. A telecommunication handshake may include exchanging signals to establish a communication link as well as to agree as to which protocols to implement. A telecommunication handshake may include negotiating parameters to be utilized between user 120 client device 112 and computing device 104, including information transfer rate, coding alphabet, parity, interrupt procedure, and/or any other protocol or hardware features. A telecommunication handshake may include but is not limited to a transmission control protocol (TCP), simple mail transfer protocol (SMTP), transport layer security (TLS), Wi-Fi protected access (WPA), and the like.

With continued reference to FIG. 1, a communication channel interface includes an audiovisual capture device. An "audiovisual capture device," as used in this disclosure, is a device used to record sound and/or images. An audiovisual capture device may include but is not limited to, a camera, a video camera, a mobile device, a recording device, a DVD player, a sensor, a television tuner, a video capture card, a universal serial bus (USB) audio and/or visual capture device, and the like. In an embodiment, an audiovisual capture device may be located within client device 112.

Still referring to FIG. 1, communication interface includes an audiovisual streaming protocol. An "audiovisual streaming protocol," as used in this disclosure, is a packet-based communication protocol that streams video and/or audio data from one device to another and vice-versa. An audiovisual streaming protocol may support a "video chat" process whereby a user 120 of computer device can see real-time or near real-time footage of human subject 116, while human subject 116 may be able to see real-time or near real-time footage of user 120 of computing device 104. User 120 of computing device 104 may include, without limitation, a doctor, physician, nurse practitioner, nurse, therapist, psychologist, medical technician, and/or any other medical professional and/or assistant thereof. Audiovisual streaming protocol may enable user 120 to perform many actions of a medical visit virtually, for instance by having human subject 116 perform measurements of height and/or weight of human subject 116, by having human subject 116 present different body parts for inspection using audiovisual capture device, or the like.

Figure 2:
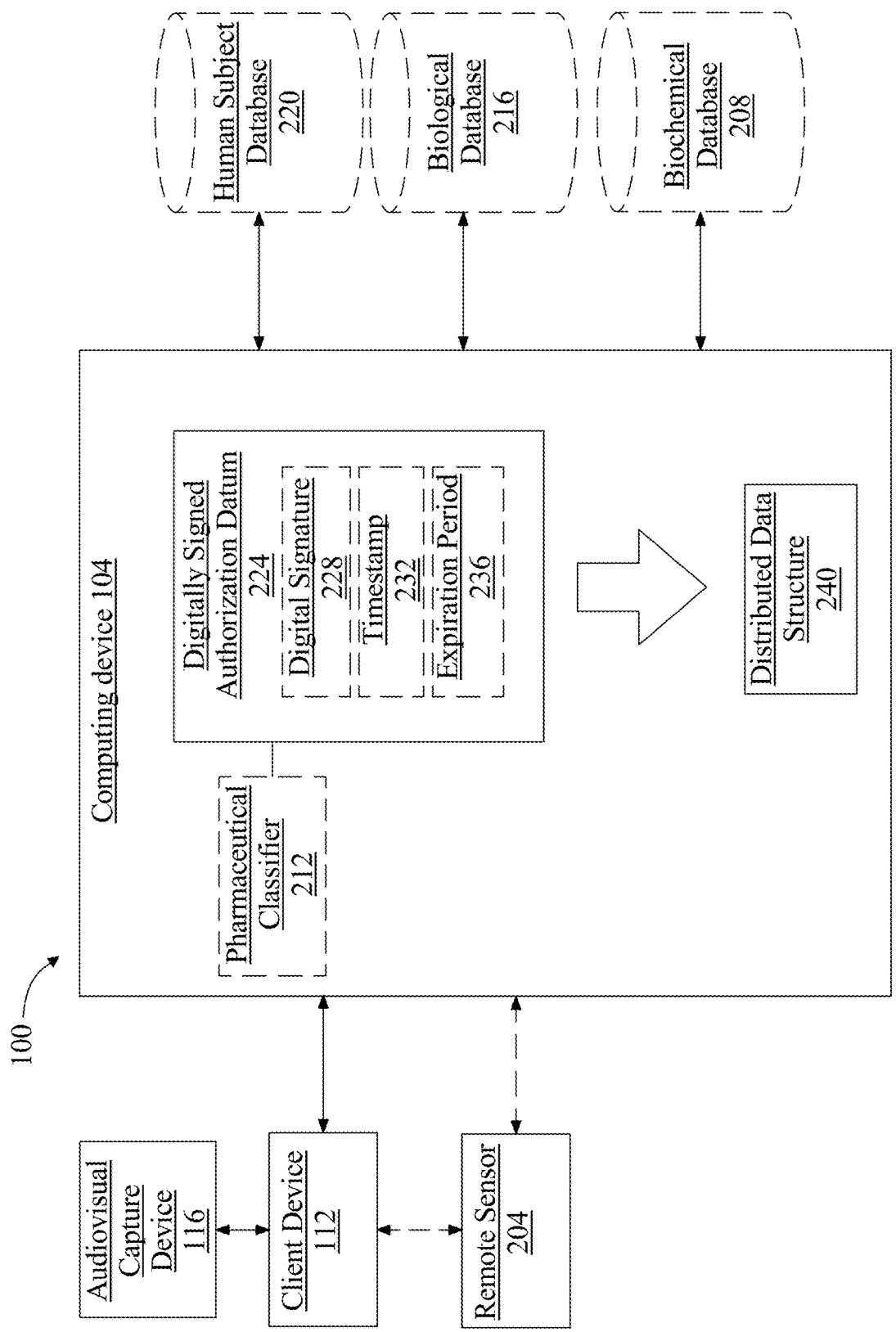
FIG. 2 is a block diagram of an exemplary embodiment of a system for cryptographically secured outputs from telemedicine sessions.

Referring now to FIG. 2, computing device 104 is configured to receive, from at least a remote sensor 204 at the second location, a plurality of current biological data associated with the human subject 116. A "remote sensor," as used in this disclosure, is a device that captures data of human subject 116 and transmits that data to computing device 104, either by transmitting the data to client device 112 which relays the data to computing device 104, or by transmitting the data separately over a network connection. "Biological data," as used in this disclosure, is data describing a physiological state and/or parameter of human subject, such as any data suitable for use in medical diagnostics, fitness measurements, or the like. Data may be transmitted via communication channel interface and/or via a separate network connection formed, for instance, using a secure sockets layer (SSL) and/or hypertext transfer protocol-secure (HTTPS) process. Remote sensor 204 may include, without limitation, a camera such as a digital camera incorporated in a mobile device or the like, a microphone such as a mobile device microphone, a motion sensor, which may include one or more accelerometers, gyroscopes, magnetometer, or the like. Remote sensor 204 may include one or more peripheral devices such as a peripheral pulse oximeter or the like. Remote sensor 204 may include a network-connected device such as a network connected digital scale or the like. In an embodiment, remote sensor 204 may be used to capture audio or visual data concerning one or more portions of human subject 116's anatomy. For instance, and without limitation, a microphone may be pressed against one or more portions of human subject 116 at direction of user 120 over communication channel, causing capture of audio data from the one or more portion of human subject 116; as a non-limiting example, audio data of human subject 116 lungs, heart, digestive system, or the like may be so captured. As a further example, user 120 may instruct human subject 116 to train a camera on one or more portions of anatomy to capture visual data concerning such one or more portions. Such biological data may be combined; for instance, audio capture of circulatory system noise data may be combined with pulse oximetry data from a peripheral pulse oximeter and/or motion-sensor data indicating a degree of activity. Remote sensor 204 may include an electrical sensor such as a portable electrocardiogram device or the like. Generally, any sensor capable of capturing data of human subject 116 and transmitting such data locally or over a network may be used as a remote sensor 204.

Still referring to FIG. 2, plurality of current biological data 208 may include cardiovascular data such as heart rate data, blood pressure data, or the like, for instance captured using audio and/or oximetry devices. Plurality of current biological data 208 may include respiratory data such as audio capture of pulmonary sounds using a microphone or the like. Plurality of current biological data 208 may include neurological data. Plurality of current biological data 208 may include digestive audio data. Plurality of biological data may include visual data captured regarding one or more elements of externally visible patient anatomy. Plurality of biological data may capture one or more elements of human subject 116 bodily motion, including gait, posture or gestural motions.

Still referring to FIG. 2, computing device 104 is configured to input, using the secure communication interface 108, an identifier of a biochemical element. In an embodiment, a "biochemical element" is a substance that has a physiological effect when ingested or otherwise introduced to a body of human subject 116. Biochemical element may include, without limitation, a pharmaceutical, drug, supplement, food, beverage, herbal remedy or other prescription or over-the-counter medication. In an embodiment, a user 120 of computing device 104, such as a physician or other medical professional; user 120 may input directly and/or may select from a drop-down list or other displayed set of options provided using secure communication interface 108. For instance, and without limitation, computing device 104 may identify a plurality of biochemical elements as a function of the plurality of current biological data displaying the plurality of biochemical elements to a user 120 of computing device 104 and receiving a command from a user 120 of the computing device 104 selecting a biochemical element of the plurality of biochemical elements. Identifying plurality of biochemical elements may be performed, without limitation, by retrieval of plurality of biochemical elements from a biochemical element database 208. Biochemical element database 208 may be implemented, without limitation, as a relational biochemical element database 208, a key-value retrieval biochemical element database 208 such as a NOSQL biochemical element database 208, or any other format or structure for use as a biochemical element database 208 that a person skilled in the art would recognize as suitable upon review of the entirety of this disclosure. Biochemical element database 208 may alternatively or additionally be implemented using a distributed data storage protocol and/or data structure, such as a distributed hash table or the like. Biochemical element database 208 may include a plurality of data entries and/or records as described above. Data entries in a biochemical element database 208 may be flagged with or linked to one or more additional elements of information, which may be reflected in data entry cells and/or in linked tables such as tables related by one or more indices in a relational biochemical element database 208. Persons skilled in the art, upon reviewing the entirety of this disclosure, will be aware of various ways in which data entries in a biochemical element database 208 may store, retrieve, organize, and/or reflect data and/or records as used herein, as well as categories and/or populations of data consistently with this disclosure.

Further referring to FIG. 2, a query of biochemical element database 208 may be generated in any manner described in this disclosure, including by submission of one or more current biological data, stored biological data, data entered by a user 120 of computing device 104, and/or data entered by human subject 116.

Figure 3:
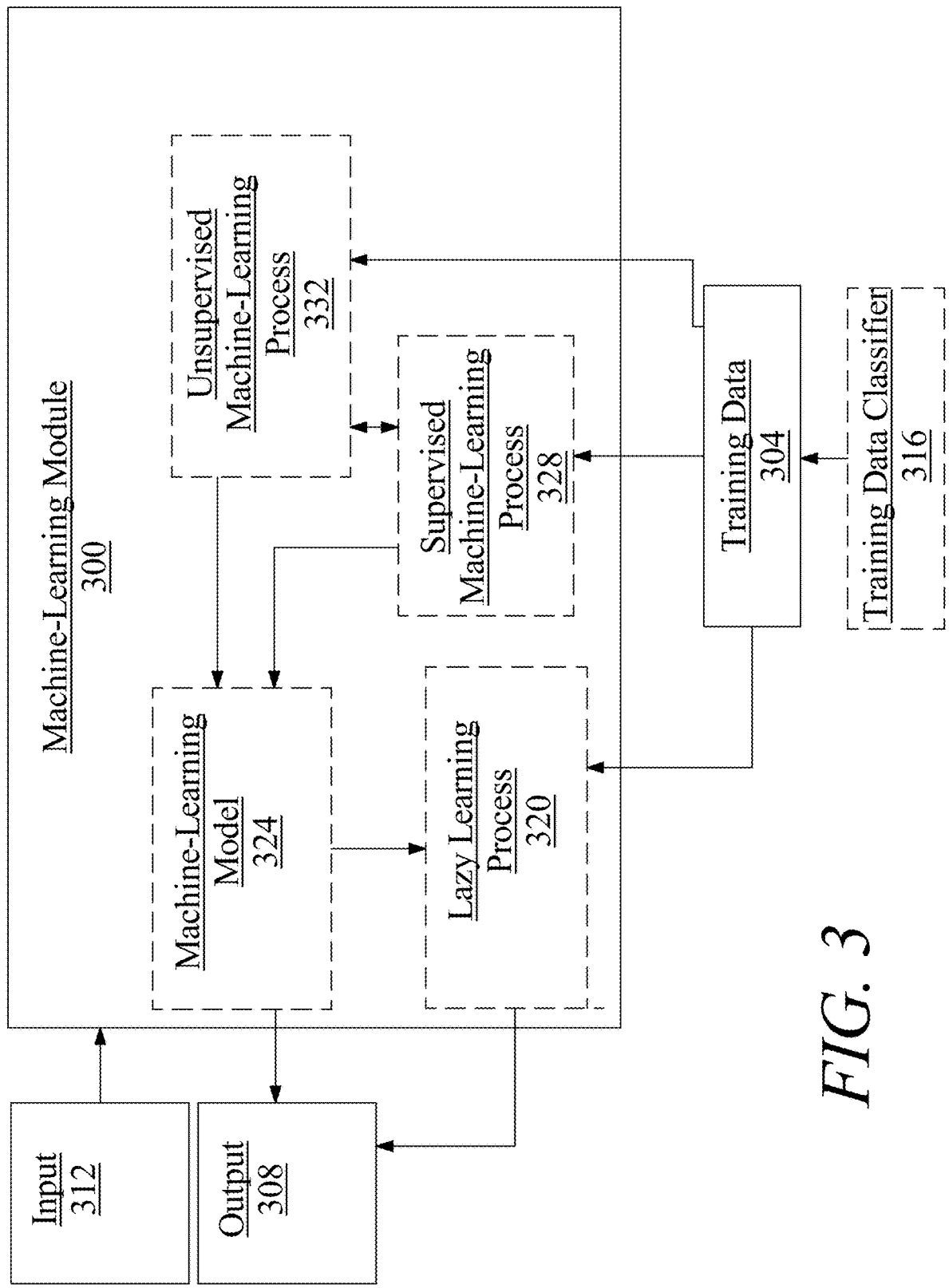
FIG. 3 is a block diagram of an exemplary embodiment of a machine-learning module.

Alternatively or additionally, computing device 104 may identify plurality of biochemical elements using a machine-learning method. Referring now to FIG. 3, an exemplary embodiment of a machine-learning module 300 that may perform one or more machine-learning processes as described in this disclosure is illustrated. Machine-learning module may include any suitable Machine-learning module may perform determinations, classification, and/or analysis steps, methods, processes, or the like as described in this disclosure using machine learning processes. A "machine learning process," as used in this disclosure, is a process that automatedly uses training data 304 to generate an algorithm that will be performed by a computing device 104/module to produce outputs 308 given data provided as inputs 312; this is in contrast to a non-machine learning software program where the commands to be executed are determined in advance by a user 120 and written in a programming language.

Still referring to FIG. 3, "training data," as used herein, is data containing correlations that a machine-learning process may use to model relationships between two or more categories of data elements. For instance, and without limitation, training data 304 may include a plurality of data entries, each entry representing a set of data elements that were recorded, received, and/or generated together; data elements may be correlated by shared existence in a given data entry, by proximity in a given data entry, or the like. Multiple data entries in training data 304 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 304 according to various correlations; correlations may indicate causative and/or predictive links between categories of data elements, which may be modeled as relationships such as mathematical relationships by machine-learning processes as described in further detail below. Training data 304 may be formatted and/or organized by categories of data elements, for instance by associating data elements with one or more descriptors corresponding to categories of data elements. As a non-limiting example, training data 304 may include data entered in standardized forms by persons or processes, such that entry of a given data element in a given field in a form may be mapped to one or more descriptors of categories. Elements in training data 304 may be linked to descriptors of categories by tags, tokens, or other data elements; for instance, and without limitation, training data 304 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 3, training data 304 may include one or more elements that are not categorized; that is, training data 304 may not be formatted or contain descriptors for some elements of data. Machine-learning algorithms and/or other processes may sort training data 304 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 304 to be made applicable for two or more distinct machine-learning algorithms as described in further detail below. Training data 304 used by machine-learning module 300 may correlate any input data as described in this disclosure to any output data as described in this disclosure.

Further referring to FIG. 3, training data may be filtered, sorted, and/or selected using one or more supervised and/or unsupervised machine-learning processes and/or models as described in further detail below; such models may include without limitation a training data classifier 316. Training data classifier 316 may include a "classifier," which as used in this disclosure is a machine-learning model as defined below, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 300 may generate a classifier using a classification algorithm, defined as a processes whereby a computing device 104 and/or any module and/or component operating thereon derives a classifier from training data 304. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 316 may classify elements of training data one or more sets and/or cohorts of persons having similar biological, demographic, or other profiles to human subject 116; training data thus classified to human subject 116 may be used to train machine-learning models, including without limitation classifiers, supervised and/or unsupervised machine-learning models, neural nets, or the like, which may include without limitation any such machine-learning models described in this disclosure.

Still referring to FIG. 3, machine-learning module 300 may be configured to perform a lazy-learning process 320 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 304. Heuristic may include selecting some number of highest-ranking associations and/or training data 304 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 3, machine-learning processes as described in this disclosure may be used to generate machine-learning models 324. A "machine-learning model," as used in this disclosure, is a mathematical and/or algorithmic representation of a relationship between inputs and outputs, as generated using any machine-learning process including without limitation any process as described above and stored in memory; an input is submitted to a machine-learning model 324 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 324 may be generated by creating an artificial neural network, such as a convolutional neural network comprising an input layer of nodes, one or more intermediate layers, and an output layer of nodes. Connections between nodes may be created via the process of "training" the network, in which elements from a training data 304 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 3, machine-learning algorithms may include at least a supervised machine-learning process 328. At least a supervised machine-learning process 328, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include inputs as described in this disclosure as inputs, outputs as described in this disclosure as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 304. Persons skilled in the art, upon reviewing the entirety of this disclosure, will be aware of various possible variations of at least a supervised machine-learning process 328 that may be used to determine relation between inputs and outputs. Supervised machine-learning processes may include classification algorithms as defined above.

Further referring to FIG. 3, machine learning processes may include at least an unsupervised machine-learning processes 332. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 3, machine-learning module 300 may be designed and configured to create a machine-learning model 324 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 3, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Still referring to FIG. 3, models may be generated using alternative or additional artificial intelligence methods, including without limitation by creating an artificial neural network, such as a convolutional neural network comprising an input layer of nodes, one or more intermediate layers, and an output layer of nodes. Connections between nodes may be created via the process of "training" the network, in which elements from a training data 304 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. This network may be trained using training data 304.

Referring again to FIG. 2, in an embodiment, computing device 104 may identify plurality of biochemical elements by receiving pharmaceutical training data correlating biological data elements to pharmaceutical data elements. Pharmaceutical training data may be input by experts such as medical researchers and/or professionals, including without limitation best practices and/or recommendations by such experts, extracted from case histories, and/or loaded from indications and/or uses approved by regulatory bodies, listed by manufacturers, or the like. Computing device 104 may train a pharmaceutical classifier 212 as a function of the pharmaceutical training data; pharmaceutical classifier 212 may be trained using any suitable classification algorithm as described above.

Still referring to FIG. 2, computing device 104 may be configured to generate a classifier using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as $P(A/B)=P(B/A) P(A) \div P(B)$, where $P(AB)$ is the probability of hypothesis A given data B also known as posterior probability; $P(B/A)$ is the probability of data B given that the hypothesis A was true; $P(A)$ is the probability of hypothesis A being true regardless of data also known as prior probability of A; and $P(B)$ is the probability of the data regardless of the hypothesis. A naïve Bayes algorithm may be generated by first transforming training data into a frequency table. Computing device 104 may then calculate a likelihood table by calculating probabilities of different data entries and classification labels. Computing device 104 may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 2, computing device 104 may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

Computing device 104 may identify the plurality of biochemical elements as a function of the pharmaceutical classifier 212 and the plurality of current biological data. For instance, and without limitation, plurality of current biological data may be directly input to pharmaceutical classifier 212 automatically; this may happen iteratively during a telemedicine session, including with iterative and/or continuous display of retrieved plurality to user 120 of computing device 104. Alternatively or additionally a user 120 of computing device 104 may select one or more of current biological data for submission to classifier and/or database. A user 120 of computing device 104 may enter additional data for pharmaceutical classifier 212 and/or database directly as text or selection of potential data and/or symptoms; for instance, identification of plurality of biochemical elements as a function of plurality of current biological data may include presentation of current biological data to user 120, who may input some or all of the data to be used in a query of biochemical element database 208 and/or pharmaceutical classifier 212. Alternatively or additionally, identification of plurality of biochemical elements as a function of plurality of current biological data may include retrieval of one or more elements of stored biological data, for instance and without limitation from a biological database 216, which may be implemented in any manner suitable for biochemical element database 208 and may store any or all biological data of and/or pertaining to human subject 116 and/or other persons; retrieval may include use of current biological data and/or data input by a user 120 of computing device 104 as elements of a query to retrieve stored biological data. As a further example, computing device 104 and/or a user 120 thereof may identify one or more conditions, such as diseases, maladies, and/or potential to suffer therefrom of human subject 116 as a function of current biological data; identification may alternatively or additionally be performed, without limitation, in any manner described in U.S. Nonprovisional application Ser. No. 16/890,686, filed on Jun. 2, 2020, and entitled "ARTIFICIAL INTELLIGENCE METHODS AND SYSTEMS FOR CONSTITUTIONAL ANALYSIS USING OBJECTIVE FUNCTIONS," the entirety of which is incorporated in this disclosure by reference. In an embodiment, pharmaceutical classifier 212 and/or biochemical element database 208 may output plurality of biochemical elements based on inputs and/or queries including an identified condition, with or without current biological data, user 120 inputs, and/or stored biological data.

Further referring to FIG. 2, computing device 104 is configured to determine, as a function of the plurality of current biological data, a tolerability of the biochemical element. "tolerability," which may alternatively be referred to as "tolerance" for the purposes of this disclosure, is ability of human subject 116 to metabolize a pharmaceutical and/or supplement and receive an intended medical benefit therefrom; this may include, without limitation, a lack of allergies or other counter-indications, an ability to metabolize using kidneys and/or liver, an ability to receive an intended therapeutic effect, or the like. In an embodiment determination of tolerance may be implemented by retrieval of tolerance data from a human subject database 220, which may be implemented in any manner suitable for implementation of a biochemical element database 208 as described above, and may contain medical records, medical history, and/or identification of allergies, adverse reactions, and/or other past data pertaining to tolerability for human subject 116 of one or more biochemical elements. Alternatively or additionally, a user 120 of computing device 104 and/or human subject 116 may enter tolerability information using secure communication interface 108. as described in U.S. Nonprovisional application Ser. No. 16/886,481, filed on May 28, 2020, and entitled METHODS AND SYSTEMS FOR OPTIMIZING SUPPLEMENT DECISIONS, the entirety of which is incorporated herein by reference. Whatever implementation used as disclosed herein, computing device 104 may use any data described above for retrieval of plurality of biochemical elements, including without limitation data entered by user 120 stored and/or current biological data, or the like; for instance, and without limitation, computing device 104 may be configured to determine the tolerability of the biochemical element by retrieving stored biological data as a function of current biological data and determining the tolerability of the biochemical element as a function of the stored biological data.

Still referring to FIG. 2, computing device 104 may be configured to authenticate plurality of current biological data and/or stored biological data biometrically. For instance, and without limitation, computing device 104 may be configured to generate at least a biometric identification signature of the human subject 116. This may be accomplished, without limitation, by receiving subject signature training data, including a plurality of category descriptors and correlated biological data entries, training a biometric signature model as a function of the subject signature training data and a machine-learning process, and generating the biometric identification signature as a function of the biometric signature model. This may be implemented, without limitation, as described in U.S. Nonprovisional application Ser. No. 16/939,408, filed on Jul. 27, 2020, and entitled "METHODS AND SYSTEMS OF BIOMETRIC IDENTIFICATION IN TELEMEDICINE USING REMOTE SENSING," the entirety of which is incorporated by reference in this disclosure. Computing device 104 may determine a degree of similarity between the stored biological data and the at least a biometric signature. Computing device 104 may authenticate the stored biological data as a function of the degree of similarity. This may be accomplished using a comparison to a preconfigured threshold value, which may be a numerical measure of degree of similarity for which passing the threshold for the purposes of authentication may require greater and/or equal similarity to that represented by the threshold. Computing device 104 may alternatively or additionally authenticate current biological data biometrically. For instance, and without limitation, computing device 104 determine a degree of similarity between the current biological data and the at least a biometric signature, for instance as described above, and authenticate the current biological data as a function of the degree of similarity. This may also, without limitation, be accomplished using a threshold comparison.

With continued reference to FIG. 2, computing device 104 is configured to generate a digitally signed authorization datum 224 as a function of the determination. A "digital signature 228," as used herein, includes a secure proof of possession of a secret by a signing device, as performed on provided element of data, known as a "message." A message may include an encrypted mathematical representation of a file or other set of data using the private key of a public key cryptographic system. Secure proof may include any form of secure proof as described above, including without limitation encryption using a private key of a public key cryptographic system as described above. Signature may be verified using a verification datum suitable for verification of a secure proof; for instance, where secure proof is enacted by encrypting message using a private key of a public key cryptographic system, verification may include decrypting the encrypted message using the corresponding public key and comparing the decrypted representation to a purported match that was not encrypted; if the signature protocol is well-designed and implemented correctly, this means the ability to create the digital signature 228 is equivalent to possession of the private decryption key and/or device-specific secret. Likewise, if a message making up a mathematical representation of file is well-designed and implemented correctly, any alteration of the file may result in a mismatch with the digital signature 228; the mathematical representation may be produced using an alteration-sensitive, reliably reproducible algorithm, such as a hashing algorithm as described above. A mathematical representation to which the signature may be compared may be included with signature, for verification purposes; in other embodiments, the algorithm used to produce the mathematical representation may be publicly available, permitting the easy reproduction of the mathematical representation corresponding to any file.

Still viewing FIG. 2, in some embodiments, digital signatures 228 may be combined with or incorporated in digital certificates. In one embodiment, a digital certificate is a file that conveys information and links the conveyed information to a "certificate authority" that is the issuer of a public key in a public key cryptographic system. Certificate authority in some embodiments contains data conveying the certificate authority's authorization for the recipient to perform a task. The authorization may be the authorization to access a given datum. The authorization may be the authorization to access a given process. In some embodiments, the certificate may identify the certificate authority. The digital certificate may include a digital signature 228.

With continued reference to FIG. 2, in some embodiments, a third party such as a certificate authority (CA) is available to verify that the possessor of the private key is a particular entity; thus, if the certificate authority may be trusted, and the private key has not been stolen, the ability of an entity to produce a digital signature 228 confirms the identity of the entity and links the file to the entity in a verifiable way. Digital signature 228 may be incorporated in a digital certificate, which is a document authenticating the entity possessing the private key by authority of the issuing certificate authority and signed with a digital signature 228 created with that private key and a mathematical representation of the remainder of the certificate. In other embodiments, digital signature 228 is verified by comparing the digital signature 228 to one known to have been created by the entity that purportedly signed the digital signature 228; for instance, if the public key that decrypts the known signature also decrypts the digital signature 228, the digital signature 228 may be considered verified. Digital signature 228 may also be used to verify that the file has not been altered since the formation of the digital signature 228.

Continuing to refer to FIG. 2, a "secure proof," as used in this disclosure, is a protocol whereby an output is generated that demonstrates possession of a secret, such as device-specific secret, without demonstrating the entirety of the device-specific secret; in other words, a secure proof by itself, is insufficient to reconstruct the entire device-specific secret, enabling the production of at least another secure proof using at least a device-specific secret. A secure proof may be referred to as a "proof of possession" or "proof of knowledge" of a secret. Where at least a device-specific secret is a plurality of secrets, such as a plurality of challenge-response pairs, a secure proof may include an output that reveals the entirety of one of the plurality of secrets, but not all of the plurality of secrets; for instance, secure proof may be a response contained in one challenge-response pair. In an embodiment, proof may not be secure; in other words, proof may include a one-time revelation of at least a device-specific secret, for instance as used in a single challenge-response exchange.

Still referring to FIG. 2, secure proof may include a zero-knowledge proof, which may provide an output demonstrating possession of a secret while revealing none of the secret to a recipient of the output; zero-knowledge proof may be information-theoretically secure, meaning that an entity with infinite computing power would be unable to determine secret from output. Alternatively, zero-knowledge proof may be computationally secure, meaning that determination of secret from output is computationally infeasible, for instance to the same extent that determination of a private key from a public key in a public key cryptographic system is computationally infeasible. Zero-knowledge proof algorithms may generally include a set of two algorithms, a prover algorithm, or "P," which is used to prove computational integrity and/or possession of a secret, and a verifier algorithm, or "V" whereby a party may check the validity of P. Zero-knowledge proof may include an interactive zero-knowledge proof, wherein a party verifying the proof must directly interact with the proving party; for instance, the verifying and proving parties may be required to be online, or connected to the same network as each other, at the same time. Interactive zero-knowledge proof may include a "proof of knowledge" proof, such as a Schnorr algorithm for proof on knowledge of a discrete logarithm. In a Schnorr algorithm, a prover commits to a randomness r, generates a message based on r, and generates a message adding r to a challenge c multiplied by a discrete logarithm that the prover is able to calculate; verification is performed by the verifier who produced c by exponentiation, thus checking the validity of the discrete logarithm. Interactive zero-knowledge proofs may alternatively or additionally include sigma protocols. Persons skilled in the art, upon reviewing the entirety of this disclosure, will be aware of various alternative interactive zero-knowledge proofs that may be implemented consistently with this disclosure.

Alternatively, and continuing to refer to FIG. 2, zero-knowledge proof may include a non-interactive zero-knowledge, proof, or a proof wherein neither party to the proof interacts with the other party to the proof; for instance, each of a party receiving the proof and a party providing the proof may receive a reference datum which the party providing the proof may modify or otherwise use to perform the proof. As a non-limiting example, zero-knowledge proof may include a succinct non-interactive arguments of knowledge (ZK-SNARKS) proof, wherein a "trusted setup" process creates proof and verification keys using secret (and subsequently discarded) information encoded using a public key cryptographic system, a prover runs a proving algorithm using the proving key and secret information available to the prover, and a verifier checks the proof using the verification key; public key cryptographic system may include RSA, elliptic curve cryptography, ElGamal, or any other suitable public key cryptographic system. Generation of trusted setup may be performed using a secure multiparty computation so that no one party has control of the totality of the secret information used in the trusted setup; as a result, if any one party generating the trusted setup is trustworthy, the secret information may be unrecoverable by malicious parties. As another non-limiting example, non-interactive zero-knowledge proof may include a Succinct Transparent Arguments of Knowledge (ZK-STARKS) zero-knowledge proof. In an embodiment, a ZK-STARKS proof includes a Merkle root of a Merkle tree representing evaluation of a secret computation at some number of points, which may be 1 billion points, plus Merkle branches representing evaluations at a set of randomly selected points of the number of points; verification may include determining that Merkle branches provided match the Merkle root, and that point verifications at those branches represent valid values, where validity is shown by demonstrating that all values belong to the same polynomial created by transforming the secret computation. In an embodiment, ZK-STARKS does not require a trusted setup.

Still referring to FIG. 2, zero-knowledge proof may include any other suitable zero-knowledge proof. Zero-knowledge proof may include, without limitation bulletproofs. Zero-knowledge proof may include a homomorphic public-key cryptography (hPKC)-based proof. Zero-knowledge proof may include a discrete logarithmic problem (DLP) proof. Zero-knowledge proof may include a secure multi-party computation (MPC) proof. Zero-knowledge proof may include, without limitation, an incrementally verifiable computation (IVC). Zero-knowledge proof may include an interactive oracle proof (IOP). Zero-knowledge proof may include a proof based on the probabilistically checkable proof (PCP) theorem, including a linear PCP (LPCP) proof. Persons skilled in the art, upon reviewing the entirety of this disclosure, will be aware of various forms of zero-knowledge proofs that may be used, singly or in combination, consistently with this disclosure.

In an embodiment, and further referring to FIG. 2, secure proof may be implemented using a challenge-response protocol. In an embodiment, this may function as a one-time pad implementation; for instance, a manufacturer or other trusted party may record a series of outputs ("responses") produced by a device possessing secret information, given a series of corresponding inputs ("challenges"), and store them securely. In an embodiment, a challenge-response protocol may be combined with key generation. A single key may be used in one or more digital signatures 228 as described in further detail below, such as signatures used to receive and/or transfer possession of crypto-currency assets; the key may be discarded for future use after a set period of time. In an embodiment, varied inputs include variations in local physical parameters, such as fluctuations in local electromagnetic fields, radiation, temperature, and the like, such that an almost limitless variety of private keys may be so generated. Secure proof may include encryption of a challenge to produce the response, indicating possession of a secret key. Encryption may be performed using a private key of a public key cryptographic system or using a private key of a symmetric cryptographic system; for instance, trusted party may verify response by decrypting an encryption of challenge or of another datum using either a symmetric or public-key cryptographic system, verifying that a stored key matches the key used for encryption as a function of at least a device-specific secret. Keys may be generated by random variation in selection of prime numbers, for instance for the purposes of a cryptographic system such as RSA that relies prime factoring difficulty. Keys may be generated by randomized selection of parameters for a seed in a cryptographic system, such as elliptic curve cryptography, which is generated from a seed. Keys may be used to generate exponents for a cryptographic system such as Diffie-Helman or ElGamal that are based on the discrete logarithm problem.

With continued reference to FIG. 2, digitally signed authorization datum 224 may include a timestamp 232 indicating a time of initiation. Timestamp 232 may be generated automatically by computing device 104; timestamp 232 may represent, without limitation, a current time as of generation of digitally signed authorization datum 224.

Digitally signed authorization datum 224 may include an expiration period 236, defined as a period in which the digitally signed authorization datum 224 is valid; expiration period 236 may be measured from the time of initiation. In an embodiment, if the authorization datum is not filled, for instance at a pharmacy, authorization datum may be treated as expired, and thus not fillable. Computing device 104 and/or other devices may automatically renew authorization datum that has not been filled. Alternatively or additionally, client device 112 may indicate that authorization datum is expiring to human subject 116, who may contact a medical professional; client device 112 may display an option that human subject 116 may select to transmit a renewal request to a medical professional, computing device 104, and/or system 100. In the latter case, computing device 104 and/or system 100 may automatically renew authorization datum; one or more parameters dictating whether or not the authorization datum may be renewed may be stored on computing device 104 and/or system 100, and/or may be entered by user 120 of computing device 104. Such parameters may include, without limitation, a maximum number of renewals, a maximum time from original generation within which renewals may be performed, or the like.

Still referring to FIG. 2, computing device 104 may be configured to post digitally signed authorization datum 224 to a distributed data structure 240. A "distributed data structure," as used in this disclosure, is a data structure having a plurality of local instances on a plurality of devices. Distributed data structure 240 may include an immutable sequential listing. An "immutable sequential listing," as used in this disclosure, is a data structure that places data entries in a fixed sequential arrangement, such as a temporal sequence of entries and/or blocks thereof, where the sequential arrangement, once established, cannot be altered or reordered. An immutable sequential listing may be, include and/or implement an immutable ledger, where data entries that have been posted to the immutable sequential listing cannot be altered.

Figure 4:
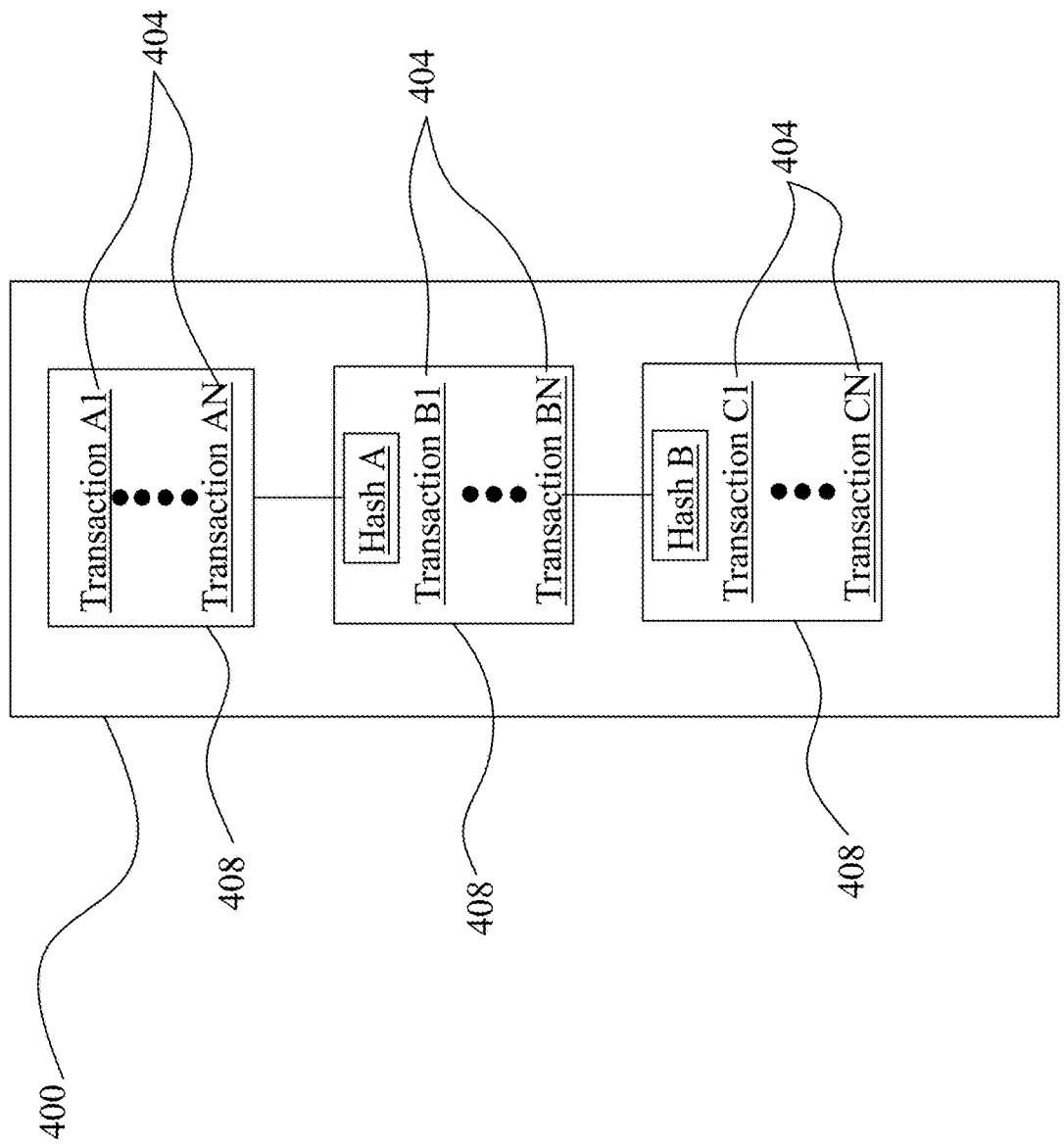
FIG. 4 is a block diagram of an exemplary embodiment of an immutable sequential listing.

Referring now to FIG. 4, an exemplary embodiment of an immutable sequential listing 400 is illustrated. Data elements are listing in immutable sequential listing 400; data elements may include any form of data, including textual data, image data, encrypted data, cryptographically hashed data, and the like. Data elements may include, without limitation, one or more at least a digitally signed assertions. In one embodiment, a digitally signed assertion 404 is a collection of textual data signed using a secure proof as described in further detail below; secure proof may include, without limitation, a digital signature 228 as described above. Collection of textual data may contain any textual data, including without limitation American Standard Code for Information Interchange (ASCII), Unicode, or similar computer-encoded textual data, any alphanumeric data, punctuation, diacritical mark, or any character or other marking used in any writing system to convey information, in any form, including any plaintext or cyphertext data; in an embodiment, collection of textual data may be encrypted, or may be a hash of other data, such as a root or node of a Merkle tree or hash tree, or a hash of any other information desired to be recorded in some fashion using a digitally signed assertion 404. In an embodiment, collection of textual data states that the owner of a certain transferable item represented in a digitally signed assertion 404 register is transferring that item to the owner of an address. A digitally signed assertion 404 may be signed by a digital signature 228 created using the private key associated with the owner's public key, as described above.

Still referring to FIG. 4, a digitally signed assertion 404 may describe a transfer of virtual currency, such as crypto currency as described below. The virtual currency may be a digital currency. Item of value may be a transfer of trust, for instance represented by a statement vouching for the identity or trustworthiness of the first entity. Item of value may be an interest in a fungible negotiable financial instrument representing ownership in a public or private corporation, a creditor relationship with a governmental body or a corporation, rights to ownership represented by an option, derivative financial instrument, commodity, debt-backed security such as a bond or debenture or other security as described in further detail below. A resource may be a physical machine e.g. a ride share vehicle or any other asset. A digitally signed assertion 404 may describe the transfer of a physical good; for instance, a digitally signed assertion 404 may describe the sale of a product. In some embodiments, a transfer nominally of one item may be used to represent a transfer of another item; for instance, a transfer of virtual currency may be interpreted as representing a transfer of an access right; conversely, where the item nominally transferred is something other than virtual currency, the transfer itself may still be treated as a transfer of virtual currency, having value that depends on many potential factors including the value of the item nominally transferred and the monetary value attendant to having the output of the transfer moved into a particular user 120's control. The item of value may be associated with a digitally signed assertion 404 by means of an exterior protocol, such as the COLORED COINS created according to protocols developed by The Colored Coins Foundation, the MASTERCOIN protocol developed by the Mastercoin Foundation, or the ETHEREUM platform offered by the Stiftung Ethereum Foundation of Baar, Switzerland, the Thunder protocol developed by Thunder Consensus, or any other protocol.

Still referring to FIG. 4, in one embodiment, an address is a textual datum identifying the recipient of virtual currency or another item of value in a digitally signed assertion 404. In some embodiments, address is linked to a public key, the corresponding private key of which is owned by the recipient of a digitally signed assertion 404. For instance, address may be the public key. Address may be a representation, such as a hash, of the public key. Address may be linked to the public key in memory of a computing device 104, for instance via a "wallet shortener" protocol. Where address is linked to a public key, a transferee in a digitally signed assertion 404 may record a subsequent a digitally signed assertion 404 transferring some or all of the value transferred in the first a digitally signed assertion 404 to a new address in the same manner. A digitally signed assertion 404 may contain textual information that is not a transfer of some item of value in addition to, or as an alternative to, such a transfer. For instance, as described in further detail below, a digitally signed assertion 404 may indicate a confidence level associated with a distributed storage node as described in further detail below.

In an embodiment, and still referring to FIG. 4 immutable sequential listing 400 records a series of at least a posted content in a way that preserves the order in which the at least a posted content took place. Temporally sequential listing may be accessible at any of various security settings; for instance, and without limitation, temporally sequential listing may be readable and modifiable publicly, may be publicly readable but writable only by entities and/or devices having access privileges established by password protection, confidence level, or any device authentication procedure or facilities described herein, or may be readable and/or writable only by entities and/or devices having such access privileges. Access privileges may exist in more than one level, including, without limitation, a first access level or community of permitted entities and/or devices having ability to read, and a second access level or community of permitted entities and/or devices having ability to write; first and second community may be overlapping or non-overlapping. In an embodiment, posted content and/or immutable sequential listing 400 may be stored as one or more zero knowledge sets (ZKS), Private Information Retrieval (PIR) structure, or any other structure that allows checking of membership in a set by querying with specific properties. Such database may incorporate protective measures to ensure that malicious actors may not query the database repeatedly in an effort to narrow the members of a set to reveal uniquely identifying information of a given posted content.

Still referring to FIG. 4, immutable sequential listing 400 may preserve the order in which the at least a posted content took place by listing them in chronological order; alternatively or additionally, immutable sequential listing 400 may organize digitally signed assertions 404 into sub-listings 408 such as "blocks" in a blockchain, which may be themselves collected in a temporally sequential order; digitally signed assertions 404 within a sub-listing 408 may or may not be temporally sequential. The ledger may preserve the order in which at least a posted content took place by listing them in sub-listings 408 and placing the sub-listings 408 in chronological order. The immutable sequential listing 400 may be a distributed, consensus-based ledger, such as those operated according to the protocols promulgated by Ripple Labs, Inc., of San Francisco, Calif., or the Stellar Development Foundation, of San Francisco, Calif., or of Thunder Consensus. In some embodiments, the ledger is a secured ledger; in one embodiment, a secured ledger is a ledger having safeguards against alteration by unauthorized parties. The ledger may be maintained by a proprietor, such as a system administrator on a server, that controls access to the ledger; for instance, the user 120 account controls may allow contributors to the ledger to add at least a posted content to the ledger but may not allow any users to alter at least a posted content that have been added to the ledger. In some embodiments, ledger is cryptographically secured; in one embodiment, a ledger is cryptographically secured where each link in the chain contains encrypted or hashed information that makes it practically infeasible to alter the ledger without betraying that alteration has taken place, for instance by requiring that an administrator or other party sign new additions to the chain with a digital signature 228. Immutable sequential listing 400 may be incorporated in, stored in, or incorporate, any suitable data structure, including without limitation any database, datastore, file structure, distributed hash table, directed acyclic graph or the like. In some embodiments, the timestamp of an entry is cryptographically secured and validated via trusted time, either directly on the chain or indirectly by utilizing a separate chain. In one embodiment the validity of timestamp is provided using a time stamping authority as described in the RFC 3161 standard for trusted timestamps, or in the ANSI ASC x9.95 standard. In another embodiment, the trusted time ordering is provided by a group of entities collectively acting as the time stamping authority with a requirement that a threshold number of the group of authorities sign the timestamp 232.

In some embodiments, and with continued reference to FIG. 4, immutable sequential listing 400, once formed, may be inalterable by any party, no matter what access rights that party possesses. For instance, immutable sequential listing 400 may include a hash chain, in which data is added during a successive hashing process to ensure non-repudiation. Immutable sequential listing 400 may include a block chain. In one embodiment, a block chain is immutable sequential listing 400 that records one or more new at least a posted content in a data item known as a sub-listing 408 or "block." An example of a block chain is the BITCOIN block chain used to record BITCOIN transactions and values. Sub-listings 408 may be created in a way that places the sub-listings 408 in chronological order and link each sub-listing 408 to a previous sub-listing 408 in the chronological order so that any computing device 104 may traverse the sub-listings 408 in reverse chronological order to verify any at least a posted content listed in the block chain. Each new sub-listing 408 may be required to contain a cryptographic hash describing the previous sub-listing 408. In some embodiments, the block chain contains a single first sub-listing 408 sometimes known as a "genesis block."

Still referring to FIG. 4, the creation of a new sub-listing 408 may be computationally expensive; for instance, the creation of a new sub-listing 408 may be designed by a "proof of work" protocol accepted by all participants in forming the immutable sequential listing 400 to take a powerful set of computing devices a certain period of time to produce. Where one sub-listing 408 takes less time for a given set of computing devices to produce the sub-listing 408 protocol may adjust the algorithm to produce the next sub-listing 408 so that it will require more steps; where one sub-listing 408 takes more time for a given set of computing devices to produce the sub-listing 408 protocol may adjust the algorithm to produce the next sub-listing 408 so that it will require fewer steps. As an example, protocol may require a new sub-listing 408 to contain a cryptographic hash describing its contents; the cryptographic hash may be required to satisfy a mathematical condition, achieved by having the sub-listing 408 contain a number, called a nonce, whose value is determined after the fact by the discovery of the hash that satisfies the mathematical condition. Continuing the example, the protocol may be able to adjust the mathematical condition so that the discovery of the hash describing a sub-listing 408 and satisfying the mathematical condition requires more or less steps, depending on the outcome of the previous hashing attempt. Mathematical condition, as an example, might be that the hash contains a certain number of leading zeros and a hashing algorithm that requires more steps to find a hash containing a greater number of leading zeros, and fewer steps to find a hash containing a lesser number of leading zeros. In some embodiments, production of a new sub-listing 408 according to the protocol is known as "mining." The creation of a new sub-listing 408 may be designed by a "proof of stake" protocol as will be apparent to those skilled in the art upon reviewing the entirety of this disclosure.

Continuing to refer to FIG. 4, in some embodiments, protocol also creates an incentive to mine new sub-listings 408. The incentive may be financial; for instance, successfully mining a new sub-listing 408 may result in the person or entity that mines the sub-listing 408 receiving a predetermined amount of currency. The currency may be fiat currency. Currency may be cryptocurrency as defined below. In other embodiments, incentive may be redeemed for particular products or services; the incentive may be a gift certificate with a particular business, for instance. In some embodiments, incentive is sufficiently attractive to cause participants to compete for the incentive by trying to race each other to the creation of sub-listings 408 Each sub-listing 408 created in immutable sequential listing 400 may contain a record or at least a posted content describing one or more addresses that receive an incentive, such as virtual currency, as the result of successfully mining the sub-listing 408.

With continued reference to FIG. 4, where two entities simultaneously create new sub-listings 408, immutable sequential listing 400 may develop a fork; protocol may determine which of the two alternate branches in the fork is the valid new portion of the immutable sequential listing 400 by evaluating, after a certain amount of time has passed, which branch is longer. "Length" may be measured according to the number of sub-listings 408 in the branch. Length may be measured according to the total computational cost of producing the branch. Protocol may treat only at least a posted content contained the valid branch as valid at least a posted content. When a branch is found invalid according to this protocol, at least a posted content registered in that branch may be recreated in a new sub-listing 408 in the valid branch; the protocol may reject "double spending" at least a posted content that transfer the same virtual currency that another at least a posted content in the valid branch has already transferred. As a result, in some embodiments the creation of fraudulent at least a posted content requires the creation of a longer immutable sequential listing 400 branch by the entity attempting the fraudulent at least a posted content than the branch being produced by the rest of the participants; as long as the entity creating the fraudulent at least a posted content is likely the only one with the incentive to create the branch containing the fraudulent at least a posted content, the computational cost of the creation of that branch may be practically infeasible, guaranteeing the validity of all at least a posted content in the immutable sequential listing 400.

Still referring to FIG. 4, additional data linked to at least a posted content may be incorporated in sub-listings 408 in the immutable sequential listing 400; for instance, data may be incorporated in one or more fields recognized by block chain protocols that permit a person or computer forming a at least a posted content to insert additional data in the immutable sequential listing 400. In some embodiments, additional data is incorporated in an unspendable at least a posted content field. For instance, the data may be incorporated in an OP_RETURN within the BITCOIN block chain. In other embodiments, additional data is incorporated in one signature of a multi-signature at least a posted content. In an embodiment, a multi-signature at least a posted content is at least a posted content to two or more addresses. In some embodiments, the two or more addresses are hashed together to form a single address, which is signed in the digital signature 228 of the at least a posted content. In other embodiments, the two or more addresses are concatenated. In some embodiments, two or more addresses may be combined by a more complicated process, such as the creation of a Merkle tree or the like. In some embodiments, one or more addresses incorporated in the multi-signature at least a posted content are typical crypto-currency addresses, such as addresses linked to public keys as described above, while one or more additional addresses in the multi-signature at least a posted content contain additional data related to the at least a posted content; for instance, the additional data may indicate the purpose of the at least a posted content, aside from an exchange of virtual currency, such as the item for which the virtual currency was exchanged. In some embodiments, additional information may include network statistics for a given node of network, such as a distributed storage node, e.g. the latencies to nearest neighbors in a network graph, the identities or identifying information of neighboring nodes in the network graph, the trust level and/or mechanisms of trust (e.g. certificates of physical encryption keys, certificates of software encryption keys, (in non-limiting example certificates of software encryption may indicate the firmware version, manufacturer, hardware version and the like), certificates from a trusted third party, certificates from a decentralized anonymous authentication procedure, and other information quantifying the trusted status of the distributed storage node) of neighboring nodes in the network graph, IP addresses, GPS coordinates, and other information informing location of the node and/or neighboring nodes, geographically and/or within the network graph. In some embodiments, additional information may include history and/or statistics of neighboring nodes with which the node has interacted. In some embodiments, this additional information may be encoded directly, via a hash, hash tree or other encoding.

With continued reference to FIG. 4, in some embodiments, virtual currency is traded as a crypto currency. In one embodiment, a crypto currency is a digital, currency such as Bitcoins, Peercoins, Namecoins, and Litecoins. Crypto-currency may be a clone of another crypto-currency. The crypto-currency may be an "alt-coin." Crypto-currency may be decentralized, with no particular entity controlling it; the integrity of the crypto-currency may be maintained by adherence by its participants to established protocols for exchange and for production of new currency, which may be enforced by software implementing the crypto-currency. Crypto currency may be centralized, with its protocols enforced or hosted by a particular entity. For instance, crypto currency may be maintained in a centralized ledger, as in the case of the XRP currency of Ripple Labs, Inc., of San Francisco, Calif. In lieu of a centrally controlling authority, such as a national bank, to manage currency values, the number of units of a particular crypto-currency may be limited; the rate at which units of crypto-currency enter the market may be managed by a mutually agreed-upon process, such as creating new units of currency when mathematical puzzles are solved, the degree of difficulty of the puzzles being adjustable to control the rate at which new units enter the market. Mathematical puzzles may be the same as the algorithms used to make productions of sub-listings 408 in a block chain computationally challenging; the incentive for producing sub-listings 408 may include the grant of new crypto currency to the miners. Quantities of crypto currency may be exchanged using at least a posted content as described above.

Referring again to FIG. 2, computing device 104 may be configured to transmit an authorization datum identifier to client device 112. Transmission may include, without limitation, posting to distributed data structure 240, which may be accessible to client device 112; a link and/or other resource locator permitting client device 112 to navigate to posting may be transmitted to the client device 112. In an embodiment, additional postings to distributed data structure 240 may be performed, e.g., by pharmacists and/or devices operated thereby and/or performing one or more roles thereof for instance, a pharmacist and/or device may post that authorization datum has been filled, that authorization datum has been renewed, or the like. This may prevent duplicate fulfillment of authorization datums, reducing a likelihood of substance abuse.

Figure 5:
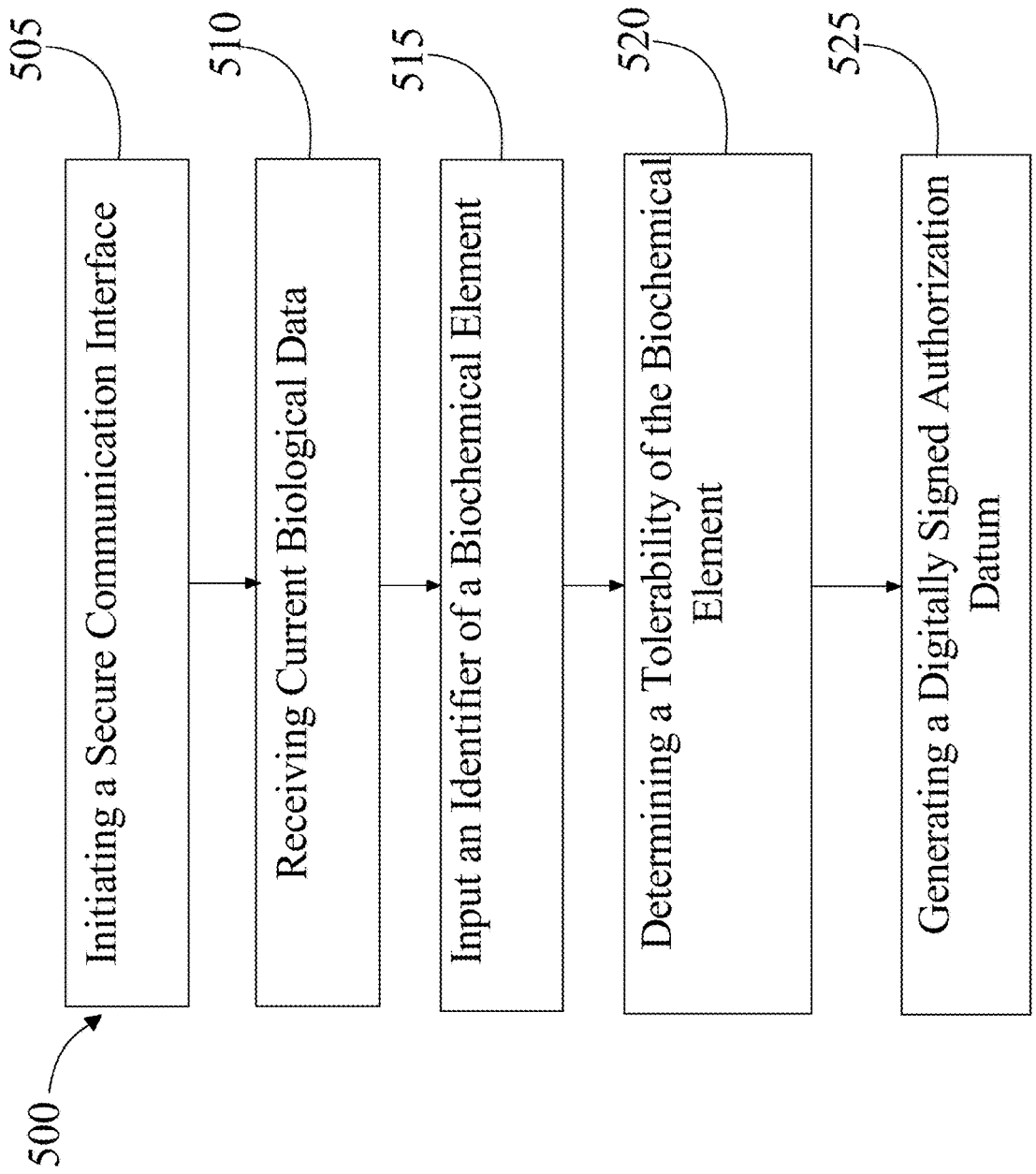
FIG. 5 is a flow diagram of an exemplary embodiment of a method of cryptographically secured outputs from telemedicine sessions.

Referring now to FIG. 5, an exemplary embodiment method 500 of telemedicine authorization datum through remote sensing. At step 505, initiating, by a computing device 104 at a first location, a secure communication interface 108 between the computing device 104 and a client device 112 associated with a human subject 116 and at a second location; this may be implemented, without limitation, as described above in reference to FIGS. 1-4.

At step 510, and still referring to FIG. 5, computing device 104 may receive, from at least a remote sensor 204 at the second location, a plurality of current biological data associated with the human subject 116; this may be implemented, without limitation, as described above in reference to FIGS. 1-4.

At step 515, and with continued reference to FIG. 5 computing device 104 may input, using the secure communication interface 108, an identifier of a biochemical element; this may be implemented, without limitation, as described above in reference to FIGS. 1-4. In an embodiment, and without limitation, inputting the identifier of the biochemical element may include identifying a plurality of biochemical elements as a function of the plurality of current biological data, displaying the plurality of biochemical elements to a user 120 of computing device 104, and receiving a command from a user 120 of the computing device 104 selecting a biochemical element of the plurality of biochemical elements. Identifying the plurality of biochemical elements may include receiving pharmaceutical training data correlating biological data elements to pharmaceutical data elements, training a pharmaceutical classifier 212 as a function of the pharmaceutical training data, and identifying the plurality of biochemical elements as a function of the pharmaceutical classifier 212.

At step 520, determining, by the computing device 104 and as a function of the plurality of current biological data, a tolerability of the biochemical element; this may be implemented, without limitation, as described above in reference to FIGS. 1-4. In an embodiment, determining the tolerability of the biochemical element may include retrieving stored biological data as a function of current biological data and determining the tolerability of the biochemical element as a function of the stored biological data. Computing device 104 may generate at least a biometric identification signature of the human subject 116, by receiving subject signature training data, including a plurality of category descriptors and correlated biological data entries, training a biometric signature model as a function of the subject signature training data and a machine-learning process, and generating the biometric identification signature as a function of the biometric signature model. Computing device 104 may determine a degree of similarity between the stored biological data and the at least a biometric signature and authenticate the stored biological data as a function of the degree of similarity, for instance as described above. The computing device 104 may authenticate current biological data, for instance by determining a degree of similarity between the current biological data and the at least a biometric signature and authenticating the current biological data as a function of the degree of similarity.

At step 525, and still referring to FIG. 5, computing device 104 is configured to generate a digitally signed authorization datum 224 as a function of the determination; this may be implemented, without limitation, as described above in reference to FIGS. 1-4. Digitally signed authorization datum 224 may include a timestamp 232 indicating a time of initiation. Digitally signed authorization datum 224 may include an expiration period 236. Computing device 104 may post digitally signed authorization datum 224 to a distributed data structure 240. Computing device 104 may transmit an authorization datum identifier to client device 112.

It is to be noted that any one or more of the aspects and embodiments described herein may be conveniently implemented using one or more machines (e.g., one or more computing devices that are utilized as a user 120 computing device 104 for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device 104) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random-access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device 104) and any related information (e.g., data structures and data) that causes the machine to perform any one of the methodologies and/or embodiments described herein.

Examples of a computing device 104 include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device 104 may include and/or be included in a kiosk.

Figure 6:
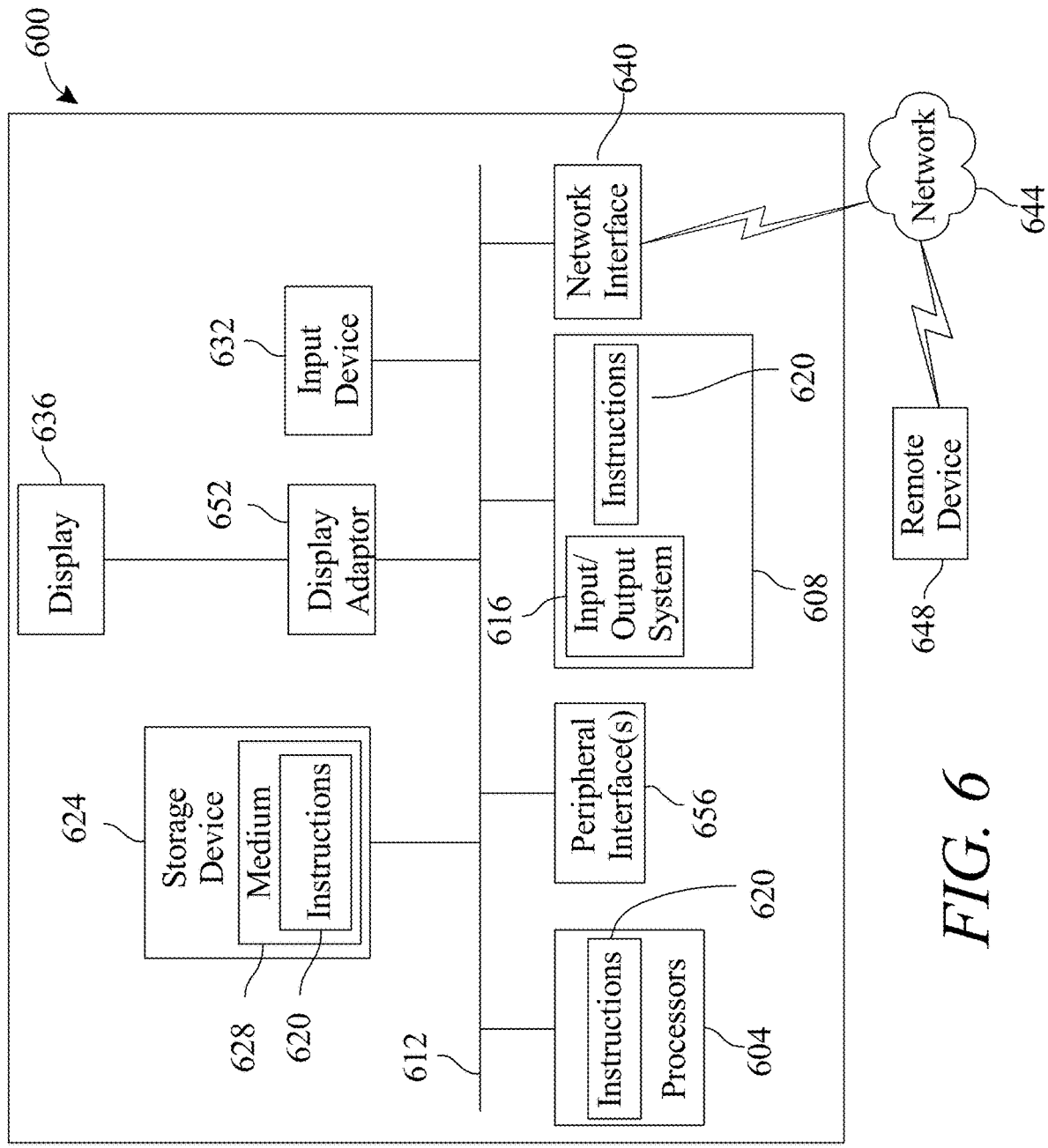
FIG. 6 is a block diagram of a computing system that can be used to implement any one or more of the methodologies disclosed herein and any one or more portions thereof.

FIG. 6 shows a diagrammatic representation of one embodiment of a computing device 104 in the exemplary form of a computer system 600 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 600 includes a processor 604 and a memory 608 that communicate with each other, and with other components, via a bus 612. Bus 612 may include any of several types of bus structures including, but not limited to, a memory bus, a memory controller, a peripheral bus, a local bus, and any combinations thereof, using any of a variety of bus architectures.

Processor 604 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 604 may be organized according to Von Neumann and/or Harvard architecture as a non-limiting example. Processor 604 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating-point unit (FPU), and/or system on a chip (SoC).

Memory 608 may include various components (e.g., machine-readable media) including, but not limited to, a random-access memory component, a read only component, and any combinations thereof. In one example, a basic input/output system 616 (BIOS), including basic routines that help to transfer information between elements within computer system 600, such as during start-up, may be stored in memory 608. Memory 608 may also include (e.g., stored on one or more machine-readable media) instructions (e.g., software) 620 embodying any one or more of the aspects and/or methodologies of the present disclosure. In another example, memory 608 may further include any number of program modules including, but not limited to, an operating system, one or more application programs, other program modules, program data, and any combinations thereof.

Computer system 600 may also include a storage device 624. Examples of a storage device (e.g., storage device 624) include, but are not limited to, a hard disk drive, a magnetic disk drive, an optical disc drive in combination with an optical medium, a solid-state memory device, and any combinations thereof. Storage device 624 may be connected to bus 612 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 624 (or one or more components thereof) may be removably interfaced with computer system 600 (e.g., via an external port connector (not shown)). Particularly, storage device 624 and an associated machine-readable medium 628 may provide nonvolatile and/or volatile storage of machine-readable instructions, data structures, program modules, and/or other data for computer system 600. In one example, software 620 may reside, completely or partially, within machine-readable medium 628. In another example, software 620 may reside, completely or partially, within processor 604.

Computer system 600 may also include an input device 632. In one example, a user 120 of computer system 600 may enter commands and/or other information into computer system 600 via input device 632. Examples of an input device 632 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 632 may be interfaced to bus 612 via any of a variety of interfaces (not shown) including, but not limited to, a serial interface, a parallel interface, a game port, a USB interface, a FIREWIRE interface, a direct interface to bus 612, and any combinations thereof. Input device 632 may include a touch screen interface that may be a part of or separate from display 636, discussed further below. Input device 632 may be utilized as a user 120 selection device for selecting one or more graphical representations in a graphical interface as described above.

A user 120 may also input commands and/or other information to computer system 600 via storage device 624 (e.g., a removable disk drive, a flash drive, etc.) and/or network interface device 640. A network interface device, such as network interface device 640, may be utilized for connecting computer system 600 to one or more of a variety of networks, such as network 644, and one or more remote devices 648 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 644, may employ a wired and/or a wireless mode of communication. In general, any network topology may be used. Information (e.g., data, software 620, etc.) may be communicated to and/or from computer system 600 via network interface device 640.

Computer system 600 may further include a video display adapter 652 for communicating a displayable image to a display device, such as display device 636. Examples of a display device include, but are not limited to, a liquid crystal display (LCD), a cathode ray tube (CRT), a plasma display, a light emitting diode (LED) display, and any combinations thereof. Display adapter 652 and display device 636 may be utilized in combination with processor 604 to provide graphical representations of aspects of the present disclosure. In addition to a display device, computer system 600 may include one or more other peripheral output devices including, but not limited to, an audio speaker, a printer, and any combinations thereof. Such peripheral output devices may be connected to bus 612 via a peripheral interface 656. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for telemedicine prescription through remote sensing, the system comprising a computing device at a first location, the computing device configured to:
   initiate a secure communication interface between the computing device and a client device associated with a human subject and at a second location, wherein initiating the secure communication interface comprises transmitting to the client device a configuration packet uniquely identifying the computing device;
   receive, from at least a remote sensor at the second location, a plurality of current physiological data associated with the human subject;
   input, using the secure communication interface, an identifier of a pharmaceutical element, wherein inputting further comprises:
      identifying a plurality of pharmaceutical elements as a function of the plurality of current physiological data, wherein identifying the plurality of pharmaceutical elements further comprises:
         receiving pharmaceutical training data correlating physiological data elements to pharmaceutical data elements;
         training, iteratively, a pharmaceutical classifier as a function of the pharmaceutical training data; and
         identifying the plurality of pharmaceutical elements as a function of the pharmaceutical classifier and the plurality of current physiological data;
      displaying the plurality of pharmaceutical elements to a user of the computing device; and
      receiving a command from a user of the computing device selecting a pharmaceutical element of the plurality of pharmaceutical elements;
   determine, as a function of the plurality of current physiological data, a tolerability of the pharmaceutical element; and
   generate a digitally signed prescription as a function of the determination.

2. The system of claim 1, wherein the computing device is configured to
   determine the tolerability of the pharmaceutical element by:
      retrieving stored physiological data as a function of current physiological data; and
      determining the tolerability of the pharmaceutical element as a function of the stored physiological data.

3. The system of claim 2, wherein the computing device is configured to:
   generate at least a biometric identification signature of the human subject, wherein
   generating further comprises:
      receiving subject signature training data, including a plurality of category descriptors and correlated physiological data entries;
      training a biometric signature model as a function of the subject signature training data and a machine-learning process; and
      generating the biometric identification signature as a function of the biometric signature model;
   determine a degree of similarity between the stored physiological data and the at least a biometric signature; and
   authenticate the stored physiological data as a function of the degree of similarity.

4. The system of claim 1, wherein the computing device is configured to:
   generate at least a biometric identification signature of the human subject, wherein
   generating further comprises:
      receiving subject signature training data, including a plurality of category descriptors and correlated physiological data entries;
      training a biometric signature model as a function of the subject signature training data and a machine-learning process; and
      generating the biometric identification signature as a function of the biometric signature model;
   determine a degree of similarity between the current physiological data and the at least a biometric signature; and
   authenticate the current physiological data as a function of the degree of similarity.

5. The system of claim 1, wherein the digitally signed prescription includes a timestamp indicating a time of initiation.

6. The system of claim 1, wherein the digitally signed prescription includes an expiration period.

7. The system of claim 1, wherein the computing device is further configured to post the digitally signed prescription to a distributed data structure.

8. The system of claim 7, wherein the distributed data structure includes an immutable sequential listing.

9. The system of claim 1, wherein the computing device is further configured to transmit a prescription identifier to client device.

10. A method of telemedicine prescription through remote sensing, the method comprising:
   initiating, by a computing device at a first location, a secure communication interface between the computing device and a client device associated with a human subject and at a second location, wherein initiating the secure communication interface comprises transmitting to the client device a configuration packet uniquely identifying the computing device;
   receiving, by the computing device and from at least a remote sensor at the second location, a plurality of current physiological data associated with the human subject;
   inputting, by the computing device and using the secure communication interface, an identifier of a pharmaceutical element, wherein inputting further comprises:
      identifying a plurality of pharmaceutical elements as a function of the plurality of current physiological data, wherein identifying the plurality of pharmaceutical elements further comprises:
         receiving pharmaceutical training data correlating physiological data elements to pharmaceutical data elements;
         training, iteratively, a pharmaceutical classifier as a function of the pharmaceutical training data; and
         identifying the plurality of pharmaceutical elements as a function of the pharmaceutical classifier;

displaying the plurality of pharmaceutical elements to a user of computing device; and receiving a command from a user of the computing device selecting a pharmaceutical element of the plurality of pharmaceutical elements;

determining, by the computing device and as a function of the plurality of current physiological data, a tolerability of the pharmaceutical element; and generating a digitally signed prescription as a function of the determination.

11. The method of claim 10, wherein determining the tolerability of the pharmaceutical element further comprises:

retrieving stored physiological data as a function of current physiological data; and determining the tolerability of the pharmaceutical element as a function of the stored physiological data.

12. The method of claim 11 further comprising:

generating at least a biometric identification signature of the human subject, wherein generating further comprises:

receiving subject signature training data, including a plurality of category descriptors and correlated physiological data entries;

training a biometric signature model as a function of the subject signature training data and a machine-learning process; and generating the biometric identification signature as a function of the biometric signature model;

determining a degree of similarity between the stored physiological data and the at least a biometric signature; and authenticating the stored physiological data as a function of the degree of similarity.

13. The method of claim 10 further comprising:

generating at least a biometric identification signature of the human subject, wherein generating further comprises:

receiving subject signature training data, including a plurality of category descriptors and correlated physiological data entries;

training a biometric signature model as a function of the subject signature training data and a machine-learning process; and generating the biometric identification signature as a function of the biometric signature model;

determining a degree of similarity between the current physiological data and the at least a biometric signature; and authenticating the current physiological data as a function of the degree of similarity.

14. The method of claim 10, wherein the digitally signed prescription includes a timestamp indicating a time of initiation.

15. The method of claim 10, wherein the digitally signed prescription includes an expiration period.

16. The method of claim 10 further comprising posting the digitally signed prescription to a distributed data structure.

17. The method of claim 16, wherein the distributed data structure includes an immutable sequential listing.

18. The method of claim 10 further comprising transmitting a prescription identifier to client device.

* * * * *